US011571220B2

(12) United States Patent
Mayer et al.

(10) Patent No.: US 11,571,220 B2
(45) Date of Patent: Feb. 7, 2023

(54) DEVICE AND METHOD FOR PUNCHING BONE (71) Applicant: Bosonic AG, Bern (CH)

(72) Inventors: Jörg Mayer, Niederlenz (CH); Andrè Schwery, Rombach (CH); Loïc Sottas, Lausanne (CH); Dominique Neuhaus, Zürich (CH)

(73) Assignee: BOSONIC AG, Bern (CH)

( * ) Notice: Subject to any disclaimer, the term of this patent is extended or adjusted under 35 U.S.C. 154(b) by 610 days.

(21) Appl. No.: 16/580,443

(22) Filed: Sep. 24, 2019

(65) Prior Publication Data
US 2020/0289132 A1 Sep. 17, 2020

(30) Foreign Application Priority Data

Mar. 11, 2019 (CH) .................................... 00295/19

(51) Int. Cl.
A61B 17/16 (2006.01)
A61B 10/02 (2006.01)
A61B 17/32 (2006.01)
A61B 17/3205 (2006.01)

(52) U.S. Cl.
CPC ........ A61B 17/1604 (2013.01); A61B 10/025 (2013.01); A61B 17/32053 (2013.01); A61B 17/320068 (2013.01); A61B 17/1633 (2013.01)

(58) Field of Classification Search
CPC ........ A61B 17/1604; A61B 17/320068; A61B 10/025
See application file for complete search history.

(56) References Cited

U.S. PATENT DOCUMENTS

| 4,515,583 | A | 5/1985 | Sorich |
| 7,608,054 | B2 | 10/2009 | Söring et al. |
| 9,888,939 | B2* | 2/2018 | Dorawa ........... A61B 17/32053 |
| 2006/0004396 | A1 | 1/2006 | Easley et al. |
| 2007/0233131 | A1* | 10/2007 | Song .................. A61B 17/1671 606/79 |
| 2010/0121197 | A1* | 5/2010 | Ota ................ A61B 17/320068 600/462 |
| 2015/0182232 | A1 | 7/2015 | Peterson et al. |
| 2020/0038052 | A1* | 2/2020 | Fujisaki ................ A61B 17/00 |

FOREIGN PATENT DOCUMENTS

| WO | 01/43620 | 6/2001 |
| WO | 2007/019870 | 2/2007 |
| WO | 2008/131884 | 11/2008 |
| WO | 2013/057179 | 4/2013 |

OTHER PUBLICATIONS

Switzerland Search Report dated Jun. 18, 2019, Application No. CH 2952019, 3 pages.
International Search Report dated May 29, 2020, Application No. PCT/EP2020/056394, 6 pages.

* cited by examiner

Primary Examiner — Andrew Yang
(74) Attorney, Agent, or Firm — Rankin, Hill & Clark LLP (57) ABSTRACT The invention resides in the field of medical technology. It relates in particular to a sonotrode suitable for use with an ultrasonic surgical instrument. The invention refers further to an ultrasonic surgical instrument for cutting or punching bones, including such a sonotrode as well as a method for manufacturing the sonotrode of the invention.

21 Claims, 8 Drawing Sheets

DEVICE AND METHOD FOR PUNCHING BONE

BACKGROUND OF THE INVENTION

Field of the Invention

The invention resides in the field of medical technology and concerns a device for punching or stamping out hard tissues such as bone tissue. It relates in particular to a sonotrode suitable to be used with an ultrasonic surgical instrument.

Description of Related Art

Among the cutting devices for cutting bone tissue, ultrasonic instruments are particularly efficient. The present invention relates to a surgical instrument for removing bone with a shaft that extends in a longitudinal direction, which at its distal end carries a sonotrode, having a distal end piece being equipped as a stamp or a blade for penetration of bones using mechanical vibration.

Surgical punches are used, for example, in autologous chondrocyte transplantation (ACT), see DGU Mitteilungen und Nachrichten 45/2002 1, "ACI und Tissue Engineering" under the auspices of the DGU and DGOOC. A laminectomy or laminotomy are surgical procedure using bone punches to remove a portion of the vertebral bone called the lamina, which is the roof of the spinal canal. Punches of this kind, also called KERRISON Bone Punches, are sold by the company Aesculap®, Tuttlingen, Germany. Nevertheless, these are not using oscillation for cutting the bone.

Another area of application for a bone punch could be arthroscopic treatments. Over the past time, arthroscopy has become one of the most popular orthopedic surgery technics, making it possible to conduct even a very complex surgery without opening a joint. Arthroscopic surgeries are widely supported by constantly improved medical devices and instruments. Today's medicine allows for using arthroscopy not only for bigger joints, like a knee or shoulder, but it is also successfully used for small joints like a wrist or ankle. One small incision is made for introduction of a camera and thus viewing the joint and the device. Additional small incisions at different points around the joint allow the surgeon to insert surgical tools to grasp, cut, grind and provide suction as needed for joint repair. Common blades for arthroscopic surgery consists of an outer hollow sheath and an inner hollow rotating cannula with corresponding windows for suction and cutting. A coating that works as a lubricant should prevent and reduces the release of metal debris when using this rotating blades against a hard surface. One complication known is heat injury to the surrounding structures. The risk is higher with a practice of re-use, because blunt blades increases the risk of heat injury and infection. Therefore most modern instruments are for single use only. WO 2013/057179 discloses a sonotrode for a surgical instrument. The sonotrode head serves as cutting device extending in a longitudinal direction. These sonotrodes have a planar blade body, with a longitudinal cutting edge.

EP 1 987 784 B1 refers to implants to be inserted into a bone, being adapted to be used as a punching tool and to a method for preparing a recess in bone. Here the sonotrode is coupled to a punching tool having a thin walled portion and serving as an implant.

Sonotrodes for an ultrasonic surgical instrument being hollow or having a distal cutting edge corresponding to the contour of a tissue area that is to be punched out and being suitable for punching out tissue areas from bone are not known.

Bone punches, on the one hand need to be equipped to cut through very dense and strong cortical bone tissue, and this at different angles (because of different access situations). On the other hand, cutting devices need to be capable of cutting deep into for example cancellous bone tissue.

SUMMARY OF THE INVENTION

It is an object of the present invention to provide an improved sonotrode for an ultrasonic surgical instrument suitable for punching out tissue areas, as well as an ultrasonic surgical instrument therefore, including an improved sonotrode and methods for manufacturing these sonotrodes. One goal to be achieved by the improved sonotrodes is a better cutting performance for cortical bone. Cortical bone is dense and compact. Thereby the reduction of heat produced during cutting of bones is envisaged. In addition, it would be favorable to be able to use a sonotrode having a distal cutting edge which corresponds to the contour of a tissue area that is to be punched out. This may be a hollow blade or a sonotrode with a long, curved cutting edge. One problem for such sonotrodes are bending movements such as oscillations out of plane which have to be avoided. At the same time a thicker blade of the sonotrode should be avoided.

A first aspect of the invention relates to a sonotrode for an ultrasonic surgical instrument being suitable for punching out tissue areas from bone, wherein the sonotrode has a head and a distal end piece, the distal end piece being equipped as a stamp for penetration of bones using mechanical vibration. The cutting edge of the punch can be located in a plane perpendicular to the longitudinal axis of the tool carrier. Alternatively, the distal end portion of the stamp may be cut slantwise. Thus the cutting edge of the punch is located in a plane that forms an angle with the longitudinal axis of the tool, wherein the angle has to be chosen in a way that the difference between the maximum and the minimum length of the blade is less than 10% of the length of the resonator (the effective length of the vibrating part). The difference between the maximum and the minimum length of the blade should be so small that no relevant difference in amplitude results. The cut may also have a parabolic shape.

An oblique cut at the distal end portion of the sonotrode is a favorite embodiment for sonotrodes used to penetrate the cortex of a bone. The oblique cut is further suitable for methods including punching out bone using only a part of a cutting edge of a hollow sonotrode. This method can be used to achieve predetermined geometries within the bone. Thus, the sonotrodes are suitable as shaver blade and as full radius resectors.

The term "proximal" as used herein refers to the nearest to the point of attachment to the housing of an ultrasonic surgical instrument or respectively to the user of that instrument. The term "distal" as used herein refers to being situated away from the point of attachment to the housing of an ultrasonic surgical instrument or respectively to the user of that instrument. The distal edge is used to punch or cut the bone. Thus, the distal end and the proximal end are opposite ends. An alternative formulation of the above embodiment is the following: a sonotrode for an ultrasonic surgical instrument, wherein the sonotrode has a head and a distal end piece, the distal end piece being equipped as a punch or blade with a distal edge being suitable for punching bone. The distal end piece of the sonotrode according to the first aspect is able to be forced through a bone or into a bone to create a hole. This means using the sonotrode according to the invention one can cut or stamp a closed curve into a bone. For cutting this curve only one cut or cutting step is necessary.

One embodiment of the first aspect of the invention refers to a sonotrode, wherein the distal end piece includes a blade whose distal cutting edge corresponds (entirely) to the contour of a tissue area that is to be punched out.

According to the invention, the sonotrode includes a head, and a distal end piece having a longitudinal axis, wherein the distal end piece is a puncturing device for penetrating into a bone. The distal end piece or the puncturing tool is arranged at the head of the sonotrode, the puncturing tool being a punch or a hollow knife. The head and the distal end piece should be oriented in a way having a common longitudinal central axis.

Another embodiment of the first aspect of the invention refers to a sonotrode, wherein the distal end piece or the blade is designed as a hollow body being open at its distal end. Thereby it is preferred that the hollow body is not rotationally symmetric. The hollow body may have the form a hollow cylinder, wherein the cross section of the cylinder is a closed curve. The cross section may be round, oval, elliptic, polygonal. A preferred embodiment refers to a sonotrode, wherein the hollow body is a hollow elliptic cylinder, in particular a hollow elliptic cylinder being open at its distal end.

The term "oval shape" or "oval" as used herein refers to a two-dimensional shape being similar to an egg or an ellipse. It also refers to a figure that resembles two semi-circles joined by a rectangle. Differentiable, not self-intersecting, convex, closed, plane curves are oval.

For cutting deeply into bone the sonotrode should be longer. But as longer as higher is the risk of torsion movement. The inventors found that a sonotrode having at least two ribs such as reinforcing ribs, avoids torsional bending and buckling. The ribs may be located on the different sides and may be symmetrically arranged, in fact axisymmetric to the central axis. The present invention refers further to a sonotrode, wherein the distal end piece or the blade is designed as body having at least a distal part being hollow wherein the distal end (front end) is open and builds a cutting edge. In accordance with a further embodiment, the sonotrode body can be configured as a hollow body (preferably a hollow cylinder) over approximately 80% of its longitudinal extent and preferably over at least the distal half of its longitudinal extent. An alternative embodiment refers to a sonotrode being solid but having a distal end piece being hollow. In this case the distal end piece may represent only up to 10 percent or even up to 5 percent of the length of the sonotrode.

A sonotrode according to the first aspect may have a stop. The stop can be provided at the distal end piece or at the proximal head of the sonotrode or at both parts. By the provision of a stop that limits the longitudinal movement to a maximum, it is possible to avoid cutting into underlying tissue not to be punched out.

Another embodiment of the first aspect of the invention refers to a sonotrode, wherein the sonotrode has at least two lateral ribs running along a longitudinal axis of the sonotrode. This ribs may also be called reinforcing or stiffening ribs. One embodiment of the first aspect of the present invention refers to a sonotrode, wherein the sonotrode has at least one lateral rib inside of the hollow distal end piece or the blade and a second lateral rib outside of the hollow distal end piece or the blade. Another embodiment of the aspect refers to a sonotrode, wherein the sonotrode or respectively the distal end piece of the sonotrode has at least two lateral ribs on each side. Alternatively, the sonotrode may have two lateral ribs being located outside of the hollow distal end piece or blade or two lateral ribs being located inside of the hollow distal end piece or blade. The sonotrode may also have four lateral ribs located outside of the hollow distal end piece or blade and/or four lateral ribs located inside of the hollow distal end piece or blade. Each rib or fin may be radially upstanding to a constant height above the blade or distal end piece. It is further preferred that two ribs are located in a way that they protrude from the same point of the circumference, one stands up inside and one outside of the hollow distal end piece or blade. It is generally preferred that the ribs are arranged symmetrically. The ribs may be located at the points where the minor axis and the major axis of an elliptic or oval cross section cuts the circumference of the hollow distal end piece.

The ribs are attached to the sonotrode and/or respectively to the distal end piece having a longitudinal, hollow form. It is preferred that the at least two ribs run along the central axis of the sonotrode. It has been found to be advantageous that the at least two ribs run along the head and the distal end piece. Nevertheless, the at least two ribs may run only along the distal end piece of the sonotrode. The ribs are preferably solid. The ribs may have a semicircular or angular cross section. The ribs should be continuously. It may have a high and/or a width of 0.05 mm to 0.5 mm. In other words the high and/or a width of the ribs is between 20-100% or even better between 25-80% of the width of the blade. By adjusting the high of the ribs, the frequency of the resonance can be adjusted. The resonance can be change in a way to differ from the working frequency. Thus, the operating frequency with load can vary in a bigger range (while maintaining the axial vibration).

It is preferred that the ribs have no sharp edges and that the transition of the ribs to the distal end piece or the blade is smooth. Therefore, it is preferred that the transition between the ribs and the blade/distal end piece surface is continuously or in form of a curvature.

Another embodiment refers to a sonotrode according to the invention, wherein the at least two ribs have a flattened distal end. Also the proximal end may be flattened. In this case the flattening out at the proximal end may be steeper than at the distal end. The ribs on the sonotrode do not have to have the same length than the sonotrode or the distal end piece of the sonotrode. One embodiment of the invention refers to a sonotrode, wherein the ribs run only along the distal end piece of the sonotrode. Another preferred embodiment of the present invention refers to a sonotrode, wherein the distal end of the at least two ribs lies in the middle third of the length of the distal end piece or blade.

The extent of the distal end piece in the longitudinal direction can lie between 10 mm and 80 mm, preferably between 15 mm and 30 mm. The largest diameter of the distal end piece can for example lie between 3 mm and 20 mm, preferably between 5 mm and 10 mm. The sonotrode including the blade may have a length of 20 to 300 mm, preferably of 150 to 250 mm.

A sonotrode according to the first aspect of the invention is particular suitable for working axial. It allows to cut or abrade in corners or foramina of bones. One preferred use is cutting osteophytes to get decompression of the spine.

The extent of the blade of a sonotrode according to the first aspect in the longitudinal direction can lie between 15 mm and 50 mm, preferably between 18 mm and 30 mm. The maximal extent of the blade in the transverse direction can for example lie between 3 mm and 35 mm. The extent in the transverse direction is regularly less than the extent in the longitudinal direction. The depth perpendicular to the longitudinal direction and the transverse direction can likewise lie between 1 mm and 30 mm. The sonotrode may have a length of 20 to 300 mm, preferably of 50 to 250 mm, and more preferably of 100 to 200 mm.

The sonotrode of the invention may be connected to an ultrasound transducer of a surgical instrument. The instrument can be provided with a feed line through which a liquid can be supplied to the sonotrode. Additionally, or as an alternative thereto, the feed line can be embodied such that a liquid is routed along the sonotrode on the outside and/or the inside.

The sonotrode of the invention may further include a sleeve with a window, which allows that only a part of the distal end of the sonotrode protrudes out of the sleeve. The sleeve may be located around the sonotrode and may be connected to the housing or handle of the ultrasonic instrument. It is preferred that the sonotrode is symmetrically attached within the sleeve. The sleeve may have a window at the distal end so that only a part of the sonotrode protrudes out of the sleeve and preferably only a part of the cross section of the distal part protrudes out. This part can be used to punch out bone. The sleeve may further be arranged in a way that it can be rotated around the sonotrode. It is preferred that the rotation can be adjusted using a scale or can be determined using a scale. The scale may be attached to the housing. By rotation it is possible to used different parts of the distal cutting edge of the sonotrode, wherein the other parts are protected. This allows to cut bone using different parts of the sonotrode and at the same time shielding other parts not be used, so that no damage is caused within surrounding tissue by parts of the sonotrode not used. The window of the sleeve may be formed to shield at least the half of the sonotrode cross section at the distal end of the sonotrode. The cross section of the sleeve may be round or may be adapted to the cross section of the sonotrode. This means the cross section may have the same form as the cross section of the sonotrode but may be a (little bit) larger.

When perforating or punching bone there are several possibilities to dispose the removed bone fragments. One possibility is to impact the cut dense bone core into the underlying trabecular bone, which is compacted so that the bleeding can be impaired. The fragments may further be aspirated or removed by special devices. Using the devices according to the present invention the bone may be removed as one bone core or fragment and not as debris. This bone core may remain within the distal end of the sonotrode. In the following the bone core may either be removed to the outside and flushed away from the operation site together with the blood etc. or it may be sucked further into a space of the sonotrode and stored until the device of the invention will be removed from the operation site. In this case the sonotrode may be a disposable article which is removed from the device and through away after each surgery together with the extracted bone. This makes a laborious cleaning of the device redundant. There is no bone debris which may obstruct a liquid supply or a suction device and has to be pushed away.

One objective of the invention is to provide a device suitable to reduce the blockage by bone debris within the instrument. The invention refers therefore to a device, wherein the sonotrode or the housing includes a void space suitable for storage of removed bone fragments. Another embodiment of the invention refers to a device, wherein the sonotrode and/or the housing includes a pipeline suitable for liquid supply to the distal cutting edge or applying vacuum to the sonotrode. Using the liquid supply it is possible to remove the bone core from the sonotrode and the vacuum is suitable to support retaining the bone core within the opening.

There may be specific elements located interior of the sonotrode which facilitates the breakage of the bone core after cutting into the dense bone. Such elements may be ribs. Cross-threading of the ribs exert force to the bone core removing it from the underlying layers of the bone tissue. Consequently, another aspect of the invention refers to a device, wherein the sonotrode includes protruding elements, such as ribs, on the inner surface suitable to exert torsion force to the cut bone. It may also be useful to shred the bone cores after being removed. Therefore the sonotrode may have slicing elements within the interior.

One field of application for sonotrodes according to the present invention is spinal surgery. The synovial joints between the superior and inferior articular processes on adjacent vertebral bodies are termed the facet joints. Each vertebra contains two facet joints. These joints allow for spine mobility, such as bending forward, standing straight, and rotating left and right. Facetectomy is a surgical procedure which may be a part of an array of procedures, such as decompression when the cervical nerve roots within the intervertebral foramina are decompressed or instrumented posterior lumbar interbody fusion (iPLIF) and transforaminal lumbar interbody fusion, a common spinal fusion surgical technique. Facetectomy is also performed to more clearly define the bony anatomy for placement of pedicle hooks and thoracic pedicle screws.

So far the facetectomy is conducted using a semilunar-shaped osteotome (or quarter-inch osteotome), identify and outline the inferior articular facet. Once the edges are outlined, bone and cartilage are removed with a curette and a rongeur. Then a small curette is used to scrape off the remaining articular cartilage of the facet joint so that bleeding bony surfaces arise. Using a sonotrode according to the invention having a trapezoid cross section adjusted to the form of the bone fragment to be removed and having a rough surface, only one instrument is sufficient and only one or two cuts are necessary for facetectomy. Therefore one embodiment refers to a sonotrode for an ultrasonic surgical instrument being suitable for facetectomy (partial or complete) or laminectomy, wherein the sonotrode has a head and a distal end piece, the distal end piece being equipped as a stamp for penetration of bones, respectively the facet joint, using mechanical vibration, wherein the distal end piece or the blade is designed as a hollow body being open at its distal end. It is preferred that the distal end piece includes a blade whose distal cutting edge is trapezoid and corresponds to the contour of a bone (and cartilage) to be punched out during facetectomy.

Another aspect of the invention refers to a method performing facetectomy including the following steps:

Exposing of an affected facet joint,
Removing the affected facet joint, and optionally
performing one further action such as a microdiscectomy or discectomy, a laminotomy or laminectomy, a foraminotomy or a foraminectomy, or a spinal fusion, wherein an ultrasonic surgical instrument with a sonotrode of the invention is used, wherein the sonotrode has a head and a distal end piece, the distal end piece being equipped as a stamp for penetration of the facet joint, using mechanical vibration, wherein the distal end piece or the blade is designed as a hollow body being open at its distal end which has a trapezoid distal cutting edge is trapezoid corresponding to the contour of bone (and cartilage) to be punched out during facetectomy. It is preferred that only one or two cuts of the instrument are sufficient for removing the facet joint and that no other instrument is required for the step "removing the affected facet joint".

Another spinal surgery the sonotrodes according the invention are useful is artificial disc replacement which is a procedure that replaces the damaged or degenerated cervical discs in the spine. Instead of fusing the vertebra together to prevent back pain, the damaged cervical disc is removed and replaced with an artificial one. It is preferred that the sonotrode used is a sonotrode for an ultrasonic surgical instrument being suitable for punching out tissue areas from bone, wherein the sonotrode has a head and a distal end piece, the distal end piece being equipped as a stamp for penetration of bones using mechanical vibration, wherein the distal end piece includes a blade whose distal cutting edge has a rectangular cross section being designed as a hollow body being open at its distal end. It is preferred that the distal end has further structures attached at its contour which corresponds to inclined teeth which may be part of the disc replacement implants.

Another aspect of the invention refers to a method for disc replacement including the following steps:
Removing a disc
Cleaning the vertebra
Optionally relieving pressure from root nerve and
Inserting an implant, in particular a disc replacement device, wherein an ultrasonic surgical instrument with a sonotrode of the invention is used, wherein the sonotrode has a head and a distal end piece, the distal end piece being equipped as a stamp for penetration of bones using mechanical vibration, wherein the distal end piece includes a blade whose distal cutting edge has a rectangular cross section being designed as a hollow body being open at its distal end. It is preferred that the distal end has further structures attached at its contour which corresponds to inclined teeth that may be part of the disc replacement implants.

A second aspect of the invention relates to a sonotrode for an ultrasonic surgical instrument having a head and a distal end piece, the distal end piece being equipped as a blade for cutting bones using mechanical vibration, wherein the blade is arched. The arched or crescent shape of the blade may be symmetrical to the longitudinal axis defined by the middle axis of the sonotrode head. In addition, the tangent that touches the curve of the blade in the point where the curve cuts the longitudinal middle axis of the sonotrode head built an acute angle of at least 5° with the tangent that touches the curve in the outermost point.

The second aspect of the present invention refers preferably to a sonotrode, wherein the sonotrode has a head and a distal end piece, the distal end piece being equipped as a punch for penetration of bones or a blade for cutting and the distal end piece has a maximal diameter being at least one and a half times the size of the diameter of the head. It is preferred that the distal end piece has a maximal diameter being at least two times and even more preferred at least three times the size of the diameter of the head.

The blade may be mainly rectangular. Nevertheless, the blade or the distal end of the blade may be curved or bent. One embodiment of the present invention refers to a sonotrode, wherein the sonotrode has a head and a distal end piece, the distal end piece being equipped as a punch for penetration of bones or a blade for cutting and the distal end piece or the cutting edge of distal end piece or respectively of the blade has a form being different from the form of the first sonotrode and having a larger diameter. It is preferred that the sonotrode according the invention has a curved blade or punch. A particular embodiment of the invention refers to a sonotrode, wherein the distal end piece includes a blade having a distal cutting edge with a form corresponding to the contour of a tissue area that is to be punched out. The cutting edge may even entirely correspond to the contour of a tissue area that is to be punched out.

The head of the sonotrode according to second aspect of the present invention is preferably formed as a (solid) circular cylinder but the blade is a rather thin part. One possibility to adapt the distal end of the head to the proximal end of the distal end piece is to include a flattening area at the distal end of the sonotrode head. Therefore, one embodiment of the invention refers to a sonotrode wherein the head has a flattened distal end. Another possibility to adapt the distal end of the head to the proximal end of the distal end piece is to include an intermediate element. One embodiment of aspect three refers to a sonotrode, wherein the distal end piece includes an intermediate element (between sonotrode head and blade). The intermediate element may also widen the diameter from the head to the diameter of the blade. The intermediate element and the blade may be made separately or may be one piece.

One embodiment of the invention, therefore, refers to a sonotrode, wherein the intermediate element includes through holes. These holes may have the form of slits or elongated recesses running parallel to the longitudinal direction of the sonotrode or perpendicular to the cutting edge. The recesses may be trough-holes.

The intermediate element is preferably an oscillating body which can oscillate with adapted impedance at the frequency of the sonotrode and can in this manner relieve the mount of oscillations or can keep it almost fully free thereof. The recesses of the oscillating body can in this respect serve to adapt the resonant frequency of the oscillating body to the frequency of the sonotrode.

The distal (cutting) end of the blade may be flattened or sharpened. Thus, one embodiment of the invention relates to a sonotrode for an ultrasonic surgical instrument having a head and a distal end piece, the distal end piece being equipped as a blade for cutting bones using mechanical vibration, wherein the blade has a sharpened distal edge as cutting edge. In another embodiment of the sonotrode according to the third aspect the corners of the distal edge are not rounded but sharp and serves as cutting edge.

A sonotrode for an ultrasonic surgical instrument having a head and a distal end piece, may be equipped with a blade having a lateral depression on each side. An alternative formulation of the above embodiment is the following: a sonotrode for an ultrasonic surgical instrument having a head and a distal end piece, the distal end piece being equipped as a blade for cutting bones using mechanical vibration, wherein the blade has a central area of reduced thickness. The depression or central area of reduced thickness may by rectangular. The depression or central area of reduced thickness may encompass 50-90% of the surface of the blade. Thus, the inventive sonotrode may include a blade having a rim surrounding the depression or central area of reduced thickness. The width of the rim may be 0.3 to 1.5 mm. One embodiment of the first aspect of the invention refers to a sonotrode wherein the lateral depressions have the same depth and are symmetrically arranged within the blade. The blade or the rim around the depression may have a constant or unvaried thickness. It is possible that the blade of the sonotrode as well as the sonotrode is symmetrically build.

Another embodiment of the first aspect of the invention refers to a sonotrode, wherein the lateral depressions have each a depth of 0.2 to 5 mm and preferably of around 0.1 mm. This means the blade has a central area where the thickness is reduced. It is preferably reduced about 0.5 to 10 mm and more preferred the thickness is reduced about 0.2 mm. Another embodiment of the first aspect of the invention refers to a sonotrode, wherein the blade of the sonotrode has rim surrounding the depression or the central area of reduced thickness and further has a groove running parallel to that rim. In other words the depression or the central area of reduced thickness of the sonotrode blade is bound by a rim and a groove inside that rim. The groove defines a level being lower than the level of the rim and the depression. It is preferred that the depression has no sharp edges and that the transition of the rim to the depression or the groove is smooth. Therefore it is preferred that the transition between the rim and the surface of the groove or respectively the depression is continuously or in form of a curvature. In case that the transition is curved, it is possible to create a defined but stable cutting edge.

Furthermore, the area of reduced thickness of a sonotrode according to the first aspect may have an elevated structure. This structure can include ribs running parallel to each other and preferably parallel to the longitudinal axis of the sonotrode blade. The ribs may also be arranged to form a grid or regular mesh. It is preferred that the cross section of the elevated structure and in particular of the at least one rib is selected in a way that the structure (or rib) does not protrude above the rim of the blade surrounding the depression. The ribs increase the stiffness of the blade and respectively the sonotrode. Nevertheless the friction is lowered and the cooling capacity is still improved. Alternatively to ribs the elevated structure may also be formed by cubes, cuboids, frustums of pyramid, cylinders (right circular cylinder, oblique circular cylinder) or of n-gonal prisms where n is between 3 and 16.

In order to reduce the torsion of the sonotrode the elevated structure in form of ribs may be oblique to the longitudinal axis of the blade. It is preferred that the ribs forms an angle with the longitudinal axis of the sonotrode or the blade of 30 to 60°. These ribs being oblique may be crossed and thus forms a grid. The distance between the ribs may be between 0.2 and 0.7 mm. The distance between the elevated structure may also be formed by cubes, cuboids, frustums of pyramid, cylinders (right circular cylinder, oblique circular cylinder) or of n-gonal prisms where n is between 3 and 16 may be between 0.2 and 1.0 mm. The height of the elevated structures is preferably between 0.1 and 0.5 mm.

Another embodiment of the first aspect of the invention refers to a sonotrode, wherein the blade of the sonotrode has channels running from the area of the depression to the edge of the blade. In other words there are channels or grooves running from the area of reduced thickness to the edge of the blade. The channels or grooves may have the same depth as the depression. It is preferred that the channels or grooves are present on each lateral side of the blade. The channels may be at corresponding position on each side or are staggered. It is preferred that the channels or grooves are open towards the surface of the blade. Therefore, they can have a semicircular or edged shape. The channels or grooves may be arranged towards the cutting edge only. They may also run towards the distal end. There may also be embodiments wherein the channels and grooves are arranges symmetrically around the depression or area of reduced thickness. There may be between 5 to 10 channels or grooves per lateral side of the blade.

The extent of the blade in the longitudinal direction can lie between 15 mm and 40 mm, preferably between 18 mm and 30 mm. The maximal extent of the blade in the transverse direction can for example lie between 20 mm and 75 mm. The extent in the longitudinal direction is regularly less than the extent in the transverse direction. The depth perpendicular to the longitudinal direction and the transverse direction can likewise lie between 1 mm and 30 mm. One embodiment of the invention relates to a sonotrode, wherein the blade of the sonotrode has a length of 15 to 40 mm. The sonotrode (including the intermediate element and the blade) can have a length of 20 to 300 mm, preferably of 150 to 250 mm. The distal end of the sonotrode may be rounded. This means that the corners of the rectangular blade are rounded. Thereby it is preferred that the radius of circular arcs forming the edges is <0.5 mm.

The following issues refers to all sonotrodes according to the invention (not to one aspect only):

The ultrasonic system may be any conventional system and will typically include a press and a vibrating acoustic element consisting of an emitter, an amplifier and a sonotrode supplied by a high-frequency generator. Longitudinal vibrations in frequencies between 20 kHz and 40 kHz with tool amplitudes between 5 μm and 50 μm are introduced into the bone under the action of force. Ultrasonic vibrations may be focused by means of special design of the components or tools.

A sonotrode according to the invention regularly includes a shaft being part of the sonotrode head. A connection to the ultrasound transducer can be established via the proximal end of the shaft. The shaft is preferably aligned in the longitudinal direction of the distal end piece. The shaft forms the proximal end of the sonotrode head; the distal end is situated opposite thereto. For connection of the sonotrode according to the invention the shaft may include or be built by a thread. Therefore, one embodiment of the invention refers to a sonotrode wherein the head has a thread at its proximal end. In addition the head of the sonotrode and the distal end piece respectively the blade are formed together as one piece or are rigidly attached to each other. Therefore the distal end of the sonotrode head may have the same cross section as the proximal end of the distal end piece or respectively the blade or a cross section adapted to the proximal end of the distal end piece. The inventors found that sonotrodes made by additive manufacturing methods, in particular using sintering (such as selective laser sintering) have some surprising advantages. The ultrasonic surgical instrument according to the invention is regularly equipped with a line by means of which a rinsing liquid (e.g. water) can be supplied to the operating field. The surface structure generated using the afore-mentioned method of manufacturing increases the cooling efficiency by that liquid. One explanation could be that the surface structure provide for and maintain a proper liquid film on the surface of the sonotrode blade. It seems that on possible effect is that pockets created by the sintering process, which are not open to the side provide for a hydrostatic cushion.

One embodiment of the present invention refers to a sonotrode, wherein the surface of the sonotrode or the surface of the distal end piece has convex microstructures. The microstructures are curved or rounded outward like the exterior of a sphere or circle. Another embodiment of the present invention refers to a sonotrode, wherein the surface of the sonotrode or the surface of the distal end piece has a roughness average Ra between 5-20 μm. Thereby surface roughness as a component of surface texture is quantified by the deviations in the direction of the normal vector of a real surface from its ideal form. The arithmetic average roughness, Ra is the arithmetic average value of filtered roughness profile determined from deviations about the center line within the evaluation length and the most widely used one-dimensional roughness parameter.

Due to the surface roughness resulting from the sintering process there are point contacts between the distal end piece and the bone. Thus a higher energy density occurs. However, the convex surface portions which arise by the grain size distribution are more stable than for example roughness structures made by sandblasting.

Consequently, one embodiment of the present invention relates to a method for manufacturing a sonotrode as defined herein, wherein the sonotrode is manufactured by using additive manufacturing method. Direct Metal Laser Sintering (DMLS) is such an additive manufacturing process suitable to be used to produce the sonotrodes according to the invention. Thereby the sonotrodes or at least the distal end pieces are built using a laser to selectively sinter (heat and fuse) a powdered metal material into layers.

An alternative method suitable for manufacture of the sonotrodes or distal end pieces thereof is shot blasting or respectively shot peening. Sandblasting is less suitable. The surface structure resulting from the sintering process of metal grains cannot be entirely described by parameter such as roughness and grain size. Nevertheless, this particular surface structure has to be proven to be advantageously. Therefore, the present invention refers to a sonotrode according to the invention, wherein the sonotrode or at least the distal end piece of the sonotrode is manufactured using additive manufacturing method such as direct metal laser sintering. In particular, the present invention refers to a sonotrode for an ultrasonic surgical instrument being suitable for punching out tissue areas from bone, wherein the sonotrode has a head and a distal end piece, the distal end piece being equipped as a stamp for penetration of bones using mechanical vibration, wherein the sonotrode or at least the blade of the sonotrode are manufactured using an additive manufacturing method such as direct metal laser sintering. The powder to be used may have an average particle diameter of 40-80 μm. In addition, the present invention refers to a sonotrode for an ultrasonic surgical instrument, wherein the sonotrode has a head and a distal end piece, the distal end piece being equipped as a punch for penetration of bones or a blade for cutting and the distal end piece has a maximal diameter being at least one and a half times the size of the diameter of the head, wherein the sonotrode or at least the blade of the sonotrode are manufactured using an additive manufacturing method such as direct metal laser sintering. The method may further include one or more steps of heat treatment. It is preferred that the surface as resulted due to the additive manufacturing is not smoothed (evened or polished). It is further preferred that the sonotrode made using additive manufacturing may be undergo heat-treatment but no smoothing procedure (smoothing of the surface).

The invention refers further to an ultrasonic surgical instrument being suitable for punching out tissue areas from bone, including a hand-piece containing an ultrasonic transducer and a sonotrode as defined herein being mechanically coupled to the transducer.

The term "ultrasonic surgical instrument" as used herein refers to a surgical instrument with an ultrasound transducer. This ultrasonic surgical instrument of the invention includes a sonotrode as described herein being connected to the ultrasound transducer. The ultrasound transducer may include a piezoelectric element, by means of which a high-frequency AC voltage is converted into a corresponding mechanical vibration. By way of example, the frequency of the vibration can lie between 20 kHz and 40 kHz.

Preferably, the ultrasound transducer or the housing of the ultrasonic surgical instrument of the invention and the head of the sonotrode (via the shaft of the head) are coupled to each other, wherein the shaft of the head is designed to transmit the vibration energy as fully as possible from its proximal end to the distal end piece or the blade of the sonotrode respectively.

Another aspect of the present invention refers to an ultrasonic surgical instrument being suitable for punching out tissue areas from bone during arthroscopy, including a hand-piece containing an ultrasonic transducer and a sonotrode as defined herein being mechanically coupled to the transducer. The invention refers also to a system of a sonotrode as described herein together with a common known catheter or arthroscopic tube. Either the sonotrode or the catheter/arthroscopic tube may be attached to a hand piece. Between the sonotrode and the catheter tube or the arthroscopic tube should be a free space. This space may be 0.2 to 1 mm width. This space may be used for a liquid which can flow along the sonotrode. The liquid may be used to cool the sonotrode, to fill the joint and/or to rinse the operation side. Alternatively the liquid may be introduced through the sonotrode being hollow and the space between sonotrode and tube may be used to suck liquid and debris of the bone out of the operational side. Therefore, the catheter or arthroscopic tube may have at least one feed line.

The sonotrode according to the invention, is preferably designed to be adapted to a vibration frequency, e.g., in the range of 20 to 40 kHz and for vibrating substantially longitudinally in a stationary wave with anti-node positions (positions with maximum amplitude) and at least one node position (position of minimum amplitude) between the two sonotrode ends.

A sonotrode according to the invention may include, in at least the most distal node position, an increased cross section. The portion extending between two node positions of the sonotrode may include a constant cross section. Adjoining the sonotrode portion of increased cross section in the most distal node position in distal and in proximal direction are sonotrode portions of lesser cross section (larger radial clearance). Transition between the differing cross sections may include a step or may be a gradual transition. The cross section of the sonotrode portion on the distal side of the portion of increased cross section may be smaller than the cross section of the sonotrode on the proximal side of the portion with increased cross section. This means that radial clearance between sonotrode and catheter or arthroscopic tube is reduced in at least one distal node position of the sonotrode.

The invention refers further to a method including
  providing an ultrasound catheter including a hand-piece containing an ultrasonic transducer and a sonotrode as defined herein being mechanically coupled to the transducer
  inserting the catheter (or arthroscopic tube) into a joint by use of conventional arthroscopic portals, and
  cutting, stamping or punching out bone within the joint using mechanical vibration.

Within this method the sonotrode located in a catheter or an arthroscopic tube can be shifted or moved relative to the catheter or tube. This means the sonotrode may be moved longitudinally in respect to the catheter or the arthroscopic tube.

Preferably, the material of the sonotrode according to the invention is a metallic material, such as e.g. stainless steel or titanium. The sonotrode or at least the distal end piece thereof may be coated with titanium nitride (TiN). Thus, the present invention refers to a sonotrode for an ultrasonic surgical instrument being suitable for punching out tissue areas from bone, wherein the sonotrode has a head and a distal end piece, the distal end piece being equipped as a stamp for penetration of bones using mechanical vibration, wherein the sonotrode or at least the distal end piece of the sonotrode is coated with titanium nitride and is preferably be manufactured using an additive manufacturing method such as direct metal laser sintering. In addition, the present invention refers to a sonotrode for an ultrasonic surgical instrument, wherein the sonotrode has a head and a distal end piece, the distal end piece being equipped as a punch for penetration of bones or a blade for cutting and the distal end piece has a maximal diameter being at least one and a half times the size of the diameter of the head wherein the sonotrode or at least the distal end piece of the sonotrode is coated with titanium nitride and is preferably be manufactured using an additive manufacturing method such as direct metal laser sintering.

It has been shown that the spherical microstructures on the surface of the sonotrode or respectively the blade may be deformed caused by the forces acting during the cutting or rasping of the bones. Therefore, it is preferred to coat the sonotrodes or blades to harden the surface. TiN has an ideal combination of hardness, toughness, adhesion and inertness, that will not blister, flake or chip during cutting or rasping bones.

Another advantages is an optimized distribution of heat along the length of the surface created by the TiN coating. In this manner, hot spots are avoided, and the heat distribution or dispersion along the length of the surgical cutting instrument prohibits concentration of heat at the cutting edge or tips of the convex microstructures on the surface as would occur with no coating or coating only at the cutting edge.

The TiN coating may be applied by environmentally safe, Physical Vapor Deposition (PVD) vacuum system. Some processes use low temperature arc vapor deposition to deposit the titanium nitride coating, but it could also be applied by high temperature sputtering or other well-known coating processes (electron beam heating or chemical vapor deposition (CVD)). In general, pure titanium is sublimed and reacted with nitrogen in a high-energy, vacuum environment. TiN film may also be produced on Ti workpieces by reactive growth (for example, annealing) in a nitrogen atmosphere.

The TiN coating is preferably applied as a thin coating of less than 5 μm, more preferably of less than 3 μm. The thin titanium nitride coating provides the blade with a hard outer surface with a low coefficient of friction.

Preferably, the connection between the head and the vibration generator is releasable and the sonotrode including the head and the distal end piece is disposable.

The ultrasonic surgical instrument according to the invention is, e.g., a hand-held device wherein a handle portion thereof houses the vibration generator being supplied with the necessary energy by a battery or through a corresponding cable connecting the hand piece to a control and supply unit. The preferred frequency for the vibration is in the ultrasonic range, preferably in the range 15 and 40 kHz or between 20 and 30 kHz and of an energy sufficient for achieving an amplitude in the micrometer range for the distal end of the perforator, between 20 and 120 μm or preferably between 60 and 100 μm.

The device according to the invention may further include a cannula or a guide shaft around the shaft and sonotrode of the ultrasonic surgical instrument. Thereby transmission of vibrational energy though the instrument shaft is to be as efficient as possible and friction between the shaft and the cannula as low as possible. This can be achieved by providing, in an axial position in which the most distal node position of the shaft is situated, a region in which radial clearance between instrument and cannula is at a minimum. This is realized by the shaft of the instrument including, at least in the most distal node position an increased cross section, and by the through opening of the cannula portion extending form the distal end portion to beyond the most distal node position of the sonotrode including a constant cross section. The shaft may further include portions of a larger cross section at other node positions. In addition also the cannula may have regions of larger cross sections at one or more node positions. It is further preferred that the arrangement including shaft and cannula has polymeric sliding surfaces to minimize friction loss. These surfaces may be formed by a polymeric ring around the distal end of the shaft or the perforator, respectively its cutting tube. The polymeric ring may be made of PEEK. Alternatively, there may be a polymeric bushing attached at the inner surface of the cannula, which can also be made of PEEK. Consequently, the region or larger cross section may be formed as polymeric attachment to the cannula or the shaft. The region of larger cross section may also have a polymeric coating.

BRIEF DESCRIPTION OF THE DRAWINGS

Exemplary embodiments of device and method according to the invention are described in further detail in connection with the appended Figures.

DESCRIPTION OF THE PREFERRED EMBODIMENTS

In all appended FIGS., same reference numerals designate same elements or similar elements serving same functions.

Figure 1:
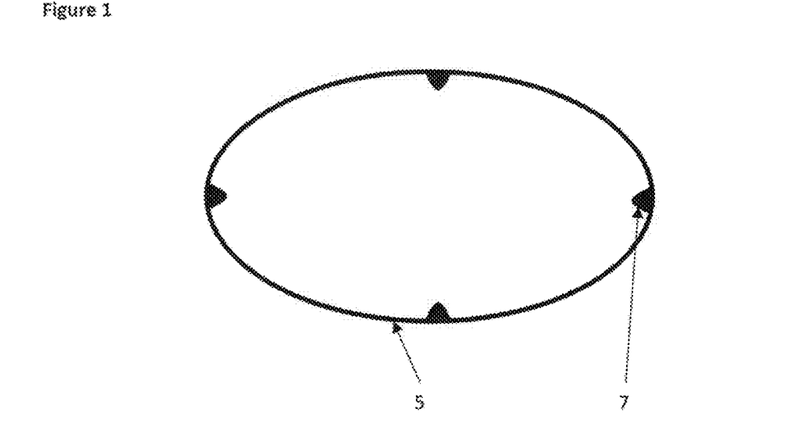
FIG. 1 shows in a schematic drawing a cross section of an exemplary embodiment of an inventive sonotrode.
Figure 2:
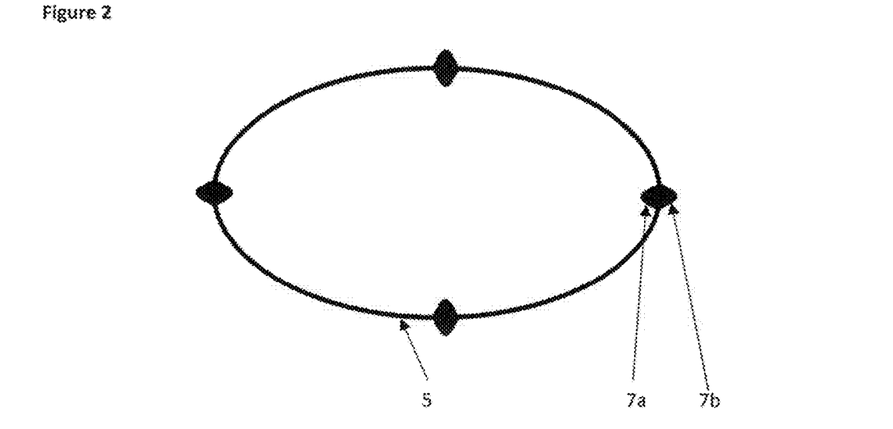
FIG. 2 shows in a schematic drawing a cross section of an exemplary embodiment of an inventive sonotrode.

FIGS. 1 and 2 illustrate each an embodiments of sonotrodes according to the first aspect of the invention. Shown is a cross section of the distal end piece 5 of the sonotrode. The distal end piece 5 is designed as a hollow elliptic cylinder being open at the very distal end. The distal end piece can serve as a punch or hollow cutting device using mechanical vibration. Therefore the very distal end of the punch or hollow cutting device may be flattened. The sonotrode or respectively the distal end piece may have lateral ribs 7. These ribs run along a longitudinal axis of the distal end piece.

The sonotrode of FIG. 1 has four ribs 7. Each rib 7 is located inside of the distal end piece. It is preferred that these ribs 7 are evenly distributed, in particular the ribs 7 are located at points where the minor axis and the major axis of the elliptic cross section cut the circumference of the cross section or respectively the surface of the distal end piece. It is also possible that the ribs 7 may each be placed at points of the circumference located half the way between the aforementioned points. Each rib 7 may be radially upstanding to a constant height above the inner surface of the distal end piece. The cross section of the ribs can vary. Here the cross section of the ribs is nearly triangular, but may also be nearly semicircular or rectangular. Nevertheless, it is generally preferred that no sharp edges at the ribs and at the transition between rib and surface of the sonotrode exist.

The sonotrode of FIG. 2 has eight ribs 7. Four ribs 7a are located inside of the distal end piece and four ribs 7b are located outside of the distal end piece. In case that a sonotrode has several ribs it has been shown to be advantageously that these ribs are placed symmetrically. It is preferred that the ribs 7 are located at the points the minor axis and the major axis of the elliptic cross section cut the circumference of the cross section or respectively the surface of the distal end piece. Each rib 7a may be radially upstanding to a constant height above the inner surface of the distal end piece and in addition each rib 7b may be radially upstanding to a constant height above the outer surface of the distal end piece. The sonotrodes according to FIGS. 1 and 2 are suitable to be used to treat spinal stenosis, in particular to trim or remove bone spurs or synovial cysts.

Figure 3:
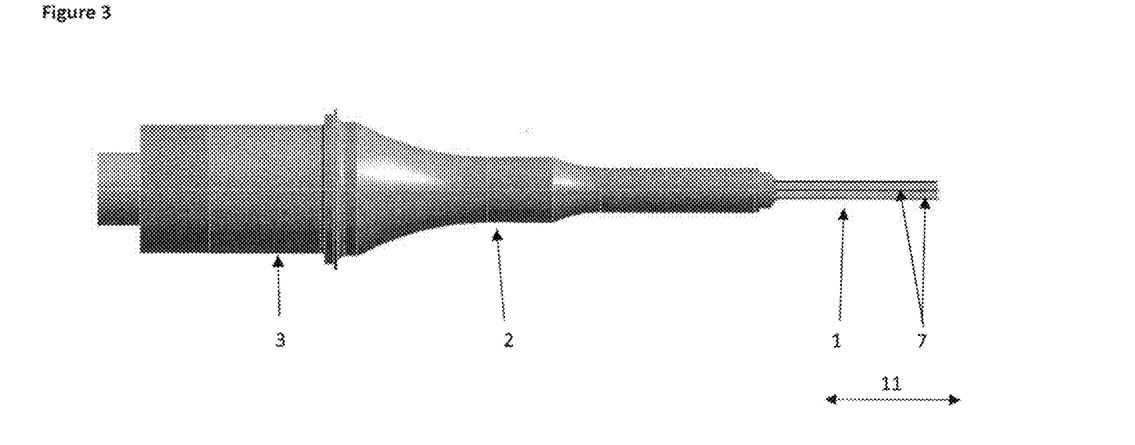
FIG. 3 shows the distal part of an ultrasonic surgical instrument for cutting bones including a piezoelectric stack located inside a housing with a sonotrode according to the invention at the tip of the housing.

FIG. 3 shows the distal part of an ultrasonic surgical instrument including a transducer, such as a piezoelectric stack 3 located inside a housing 2 with a sonotrode 1 at the tip of the housing. The sonotrode 1 has been attached to the housing 2 via its proximal end of the head. Therefore the head may have a thread or a plug-in connector at its proximal end. The sonotrode 1 connected to the housing may have longitudinal ribs 7. The ribs 7 may be located only on the distal end piece of the sonotrode and not on the head of the sonotrode as shown here. The sonotrode 1 may be a sonotrode according to FIG. 1 or 2 having an oval or elliptic cross section. However it is preferred that the cross section does not vary over the length of the sonotrode 1. The direction of oscillation is indicated by arrow 11.

Figure 4:
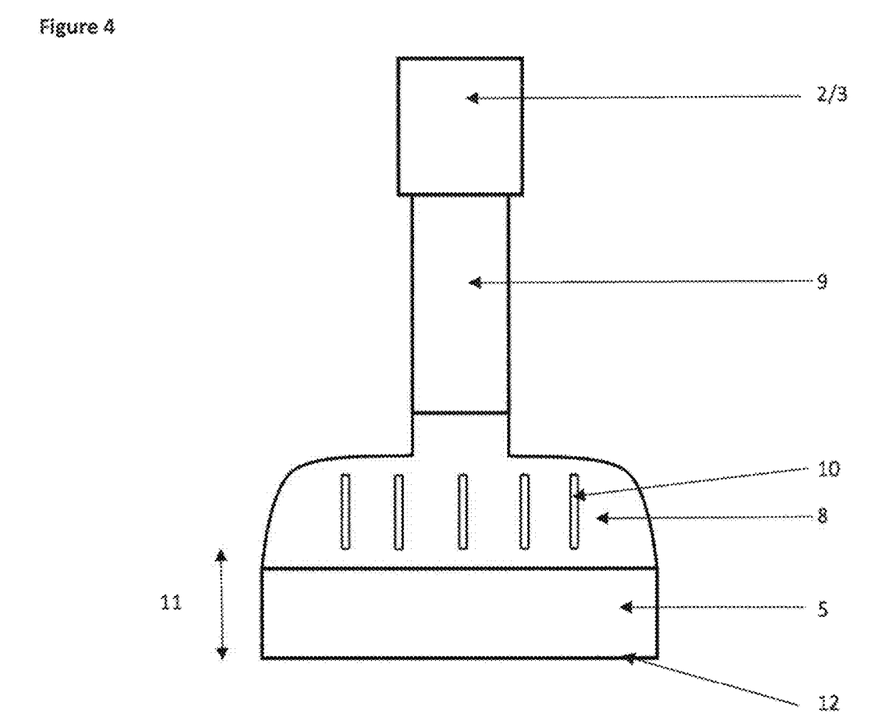
FIG. 4 shows a schematic drawing of an exemplary embodiment of an inventive sonotrode.

FIG. 4 shows a schematic side view of a sonotrode arrangement including a piezoelectric stack 3 (not shown) located inside a housing 2 coupled to a sonotrode according to the second aspect of the invention. The head of the sonotrode consist mainly of an efferent sonotrode 9 which may be formed as a solid rod. At the distal end of the sonotrode head 9 follows an intermediate element 10, which may be a separate part or a main body when produced one piece with the blade 5. The sonotrode blade 5 includes elongate holes 10 (through slits) in the direction of oscillation 11. In addition the blade 5 may be tapered towards the cutting edge 12. The width of the blade is about 5 times the size of the diameter of the sonotrode head 9. The intermediate element or the main body may have a thickness of 5-12 mm at the point of connection to the element 9 which thickness tapers down to 2-6 mm for the cutting edge 12 of blade 5, of which the width may be between 10-60 mm The blade 5 may have a straight cutting edge 12. Nevertheless, the cutting edge is preferably formed having the contour of the area to be cut or stamped out. The intermediate element 10 is used to transfer the oscillation towards the blade and the cutting edge. The intermediate element may be a booster or it may just the main body of the blade 5. In addition the intermediate element includes the expansion of the width and the transition to the form of the cutting edge.

Figure 5:
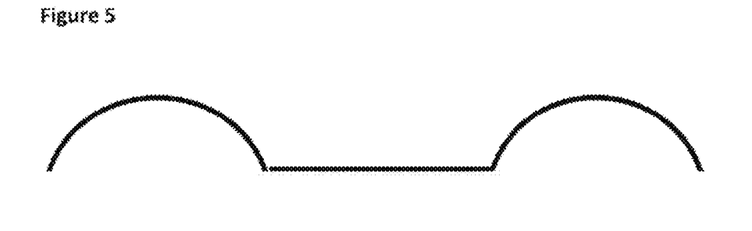
FIG. 5 shows in a schematic drawing a cross section of an exemplary embodiment of an inventive sonotrode.
Figure 6:
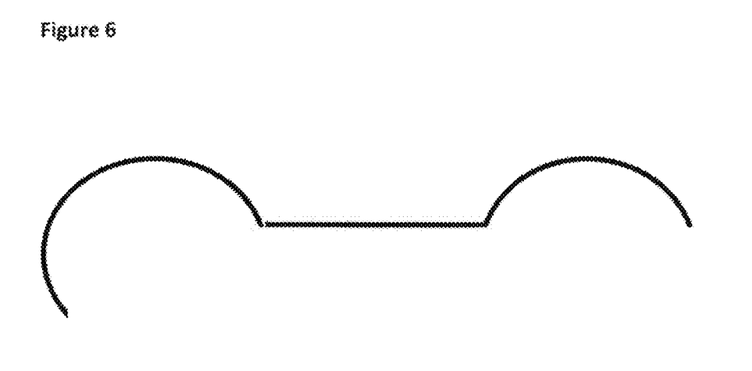
FIG. 6 shows in a schematic drawing a cross section of an exemplary embodiment of an inventive sonotrode.
Figure 7:
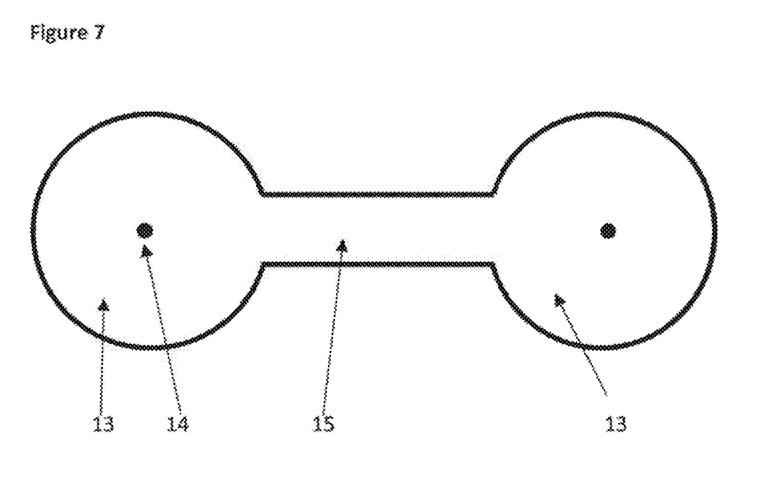
FIG. 7 shows in a schematic drawing a cross section of an implant which may be cut out using a sonotrode according to FIG. 5 or 6.

FIGS. 5 and 6 show each a schematic top view for the cutting edge of a blade of an exemplary sonotrode according to the second aspect of the invention. Both blades are adapted to cut out an implant as shown in FIG. 7. FIG. 7 shows a cross section of an implant to be removed with the aid of sonotrodes having blades as illustrated in FIGS. 5 and 6. The implant is a dual-anchor with two pin-shaped anchorage portions 13 and a stabilization portion 14 situated between the two anchorage portions 13. It may be used as a fusion device particularly suited for fusion of a human lumbar facet joint. The blade as shown in FIG. 5 is formed to have the contour of one half of the implant. This means the sonotrode has to be used twice (once on each side of the implant) to stamp out the implant after being implanted and ingrown into the bone. The blade as shown in FIG. 6 is formed to encompass at one lateral side a slightly more than half of the contour of the implant to be stamped out. Thus, it can be ensured that there is an overlap of the cuttings, when using the sonotrodes twice, once on each side.

Figure 8:
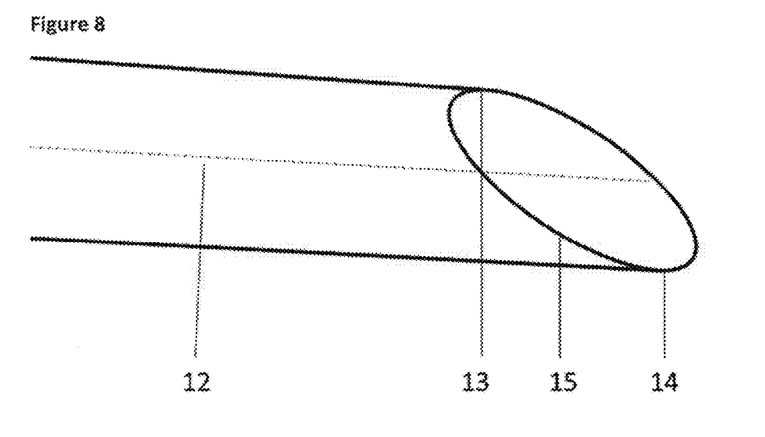
FIG. 8 shows in a schematic drawing an exemplary embodiment of an inventive sonotrode with a slanting cut.
Figure 9:
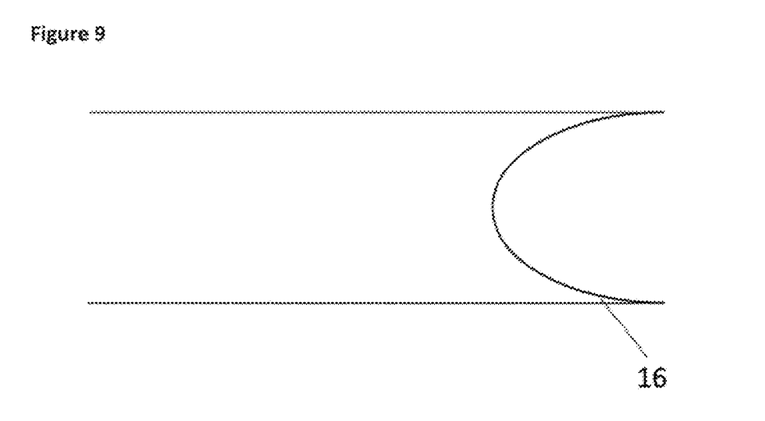
FIG. 9 shows in a schematic drawing an exemplary embodiment of an inventive sonotrode with a parabolic cut.

FIG. 8 shows a sonotrode with a distal end piece being hollow and having a slanted cut 15. The distal end portion of the electrode is cut slantwise. Thus the cutting edge of the punch is located in a plane that forms an angle with the longitudinal axis 12 of the sonotrode. The distance between the maximum 14 and the minimum length 13 of the distal end portion or the blade is less than 10% of the length of the resonator (the effective length of the vibrating part). FIG. 9 shows a sonotrode with a distal end piece having a parabolic cut 16 at the distal end.

Figure 10:
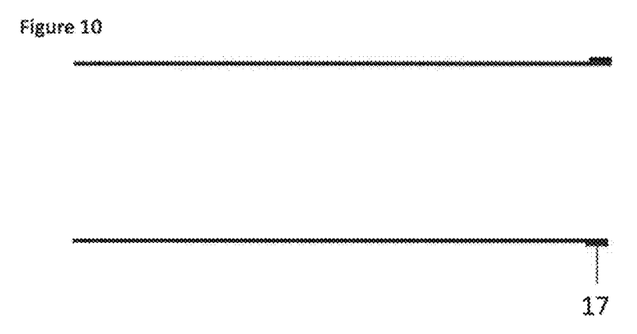
FIG. 10 shows in a schematic drawing an exemplary embodiment of an inventive sonotrode with a rim.
Figure 11:
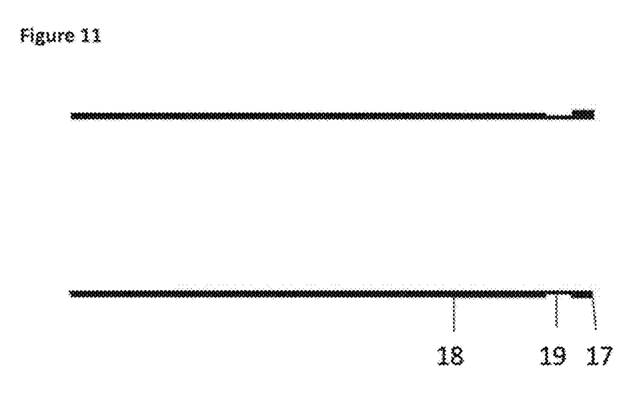
FIG. 11 shows in a schematic drawing an exemplary embodiment of an inventive sonotrode with a rim.

FIGS. 10 and 11 show each an axial sections of alternative distal end pieces of an inventive sonotrode. The sonotrode according to FIG. 10 has a rim 17. The rim 17 at the distal end of the sonotrode according to FIG. 11 bounds a depression. The depression consists of a groove 19 which runs parallel to the rim 17. The area 18 proximal to the rim 17 and the groove 19 is elevated in regard to the groove 19 but low-rise compared to the rim 17. The area 18 may be between 0.1 and 5 µm lower than the rim 17. The groove 19 may be between 0.2 and 5 µm lower than the area 18. The minimal depth of the area 18 is sufficient to adequately lower the friction.

The rim 17 may also be formed with a curvature or parabolic. The width of the rim may be <1 mm and preferably between 0.2-0.5 mm. The rim 17 runs preferably perpendicular to the longitudinal axis of the sonotrode.

Figure 12:
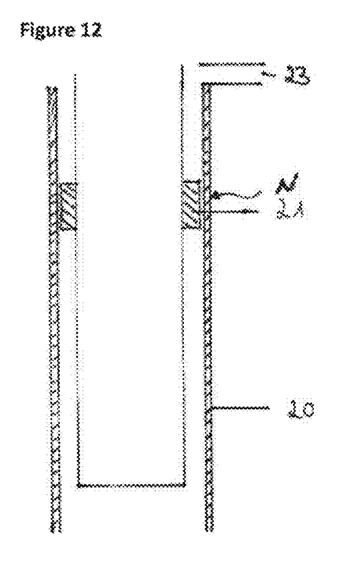
FIG. 12 shows in a schematic drawing an exemplary embodiment of an inventive sonotrode within an arthroscopic tube.

FIG. 12 shows in an axial section a distal part of a sonotrode within an arthroscopic tube 20. The sonotrode can be moved in a distal direction relative to the tube 20. Within tube 20 is a lumen being all in all a lumen as used for the optical instruments (camera) used within an arthroscopy. The sonotrode is equipped with a portion 21 of a larger cross section in the node position N. This larger cross section is caused by a ring around the sonotrode wall. This ring may be a polymeric ring or a ring made of the same material as the sonotrode.

The arthroscopic tube may include a supply 23 for a liquid which may be used to cool the sonotrode, to fill the joint and/or to flush the operating side of the sonotrode. The liquid should be sterile and may be physiological saline solution.

Figure 13:
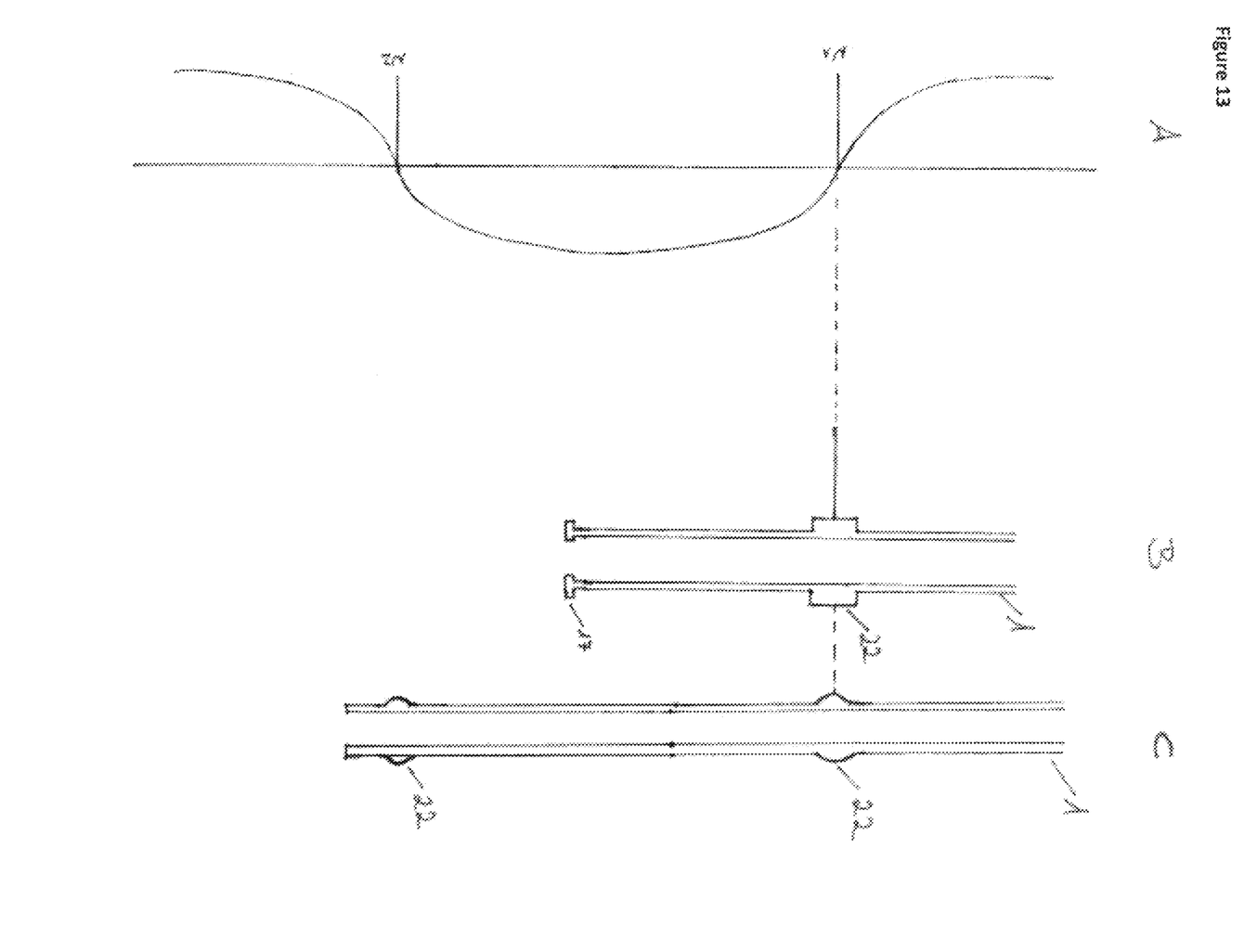
FIG. 13 illustrates two examples of the sonotrode (B and C) according to the invention.

FIGS. 13 B and C are axial sections and show each a distal portion of a sonotrode, which is adapted to a selected vibration frequency to vibrate with a node position N. FIG. 13 A illustrates the vibration of the sonotrode with nodes N1 and N2.

An arthroscopic tube (not shown) reaches distally to cover the distal end of the sonotrode 1. The sonotrode 1 is equipped with a portion 22 of a larger cross section in the node position N. The larger cross section is caused by a bulge of the wall of the sonotrode. The bulge may be an integral part of the sonotrode wall and can be formed as a ring around the sonotrode having a square cross section (FIG. 13 B). Alternatively, there may be several rectangles sitting on one cycle around the sonotrode with some space between them. These rectangles can be arranged within a consistent interval on that circle. Instead of rectangles there may also be spherical bulges attached on one circle around the sonotrode. The circle is always located in a node position N.

Figure 14:
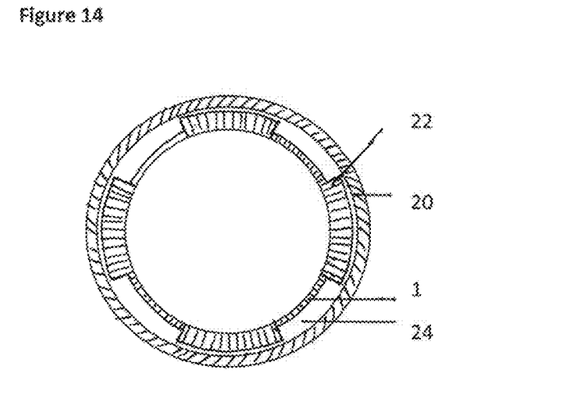
FIG. 14 shows a cross section of a sonotrode according to FIG. 13 B located within an arthroscopic tube.

FIG. 14 shows a cross section of the sonotrode according to FIG. 13 B in the node position N1. The sonotrode 1 is located within an arthroscopic tube 20. As can be seen, four rectangle bulges causes a larger cross section of the sonotrode in the node position N. Between these bulges is space 24, which may serve as channel for a liquid (cooling/flushing). Alternatively, the liquid may flow through the lumen of the sonotrode 1 and the space 24 may be used to suck liquid and debris.

Figure 15:
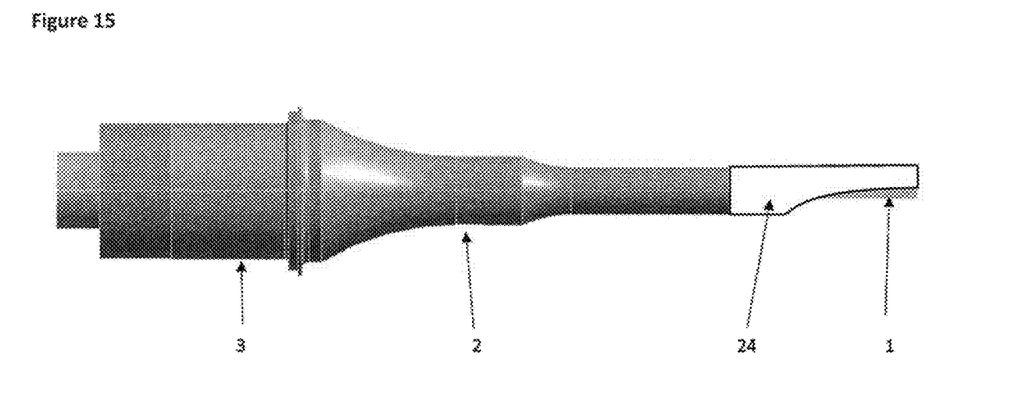
FIG. 15 shows the distal part of an ultrasonic surgical instrument.

FIG. 15 shows the distal part of an ultrasonic surgical instrument including a transducer 3 located inside a housing 2 with a sonotrode 1 at the tip of the housing. The sonotrode 1 has been attached to the housing 2 via its proximal end of the head. The device may further include a sleeve 24 around the sonotrode 1 which may be connected to the housing. The sonotrode 1 may be each sonotrode according to the present invention. It is preferred that the sonotrode is symmetrically. The sleeve may have a window at the distal end so that only a part of the sonotrode protrudes out of the sleeve. Therefore the window is like a longitudinal cut starting at the distal edge and ending in a curve leveling off. Alternatively the window is a like a cut cutting away a part of the cross section from the sleeve. The window of the sleeve 24 may be formed to shield at least the half of the sonotrode cross section at the distal end of the sonotrode.

Figure 16:
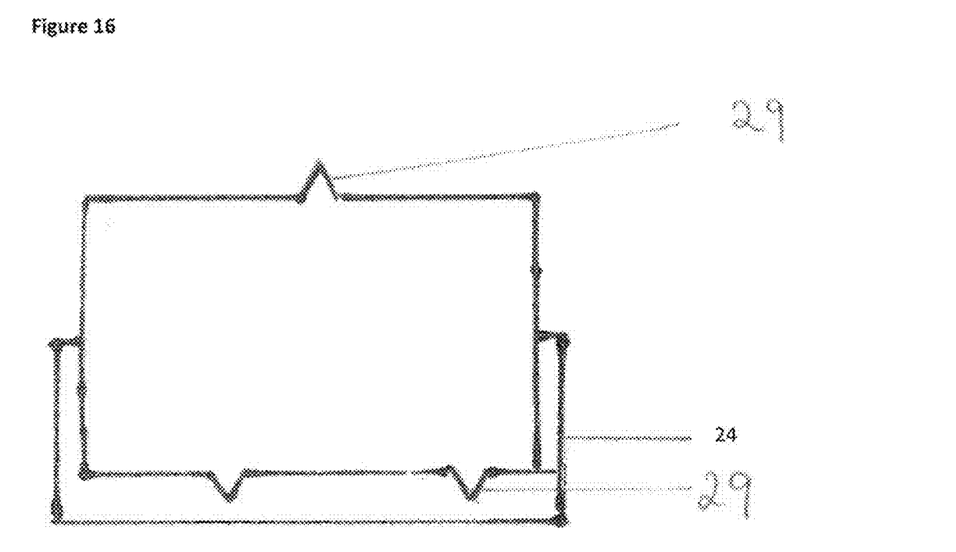
FIG. 16 shows the cross section of an exemplary embodiment of an inventive sonotrode.

FIG. 16 shows the cross section of an embodiment of a sonotrode according to the invention. This sonotrode is particularly suitable to be used during total disc replacement surgery. The sonotrode as shown in FIG. 16 may be used for preparation of a vertebral body before implantation of a disc replacement implant or artificial disc. It may also be used for removing the problematic or damaged disc and/or to clean the space between the vertebral bodies. The most commonly used total disc replacement designs have two plates. One attaches to the vertebrae above the disc being replaced and the other to the vertebrae below. The plates have an essentially planar level, side or area to come into contact with the vertebral body. Nevertheless the vertebral body are not planar. Therefore, the surgeon may cut the vertebral body. It is preferred that the cross section of the sonotrode is (essentially) rectangular or has at least one planar side. These plates may have inclined teeth for generating stability. Therefore the sonotrode may have structures 29 attached to the distal end corresponding to the inclined teeth of the plates. Alternatively the distal end piece may have a cross section including structures 29 corresponding to such teeth. The structures 29 may be ribs attached to the sonotrode having a triangular cross section or the cross section of the sonotrode may include triangular bulges.

Figure 17:
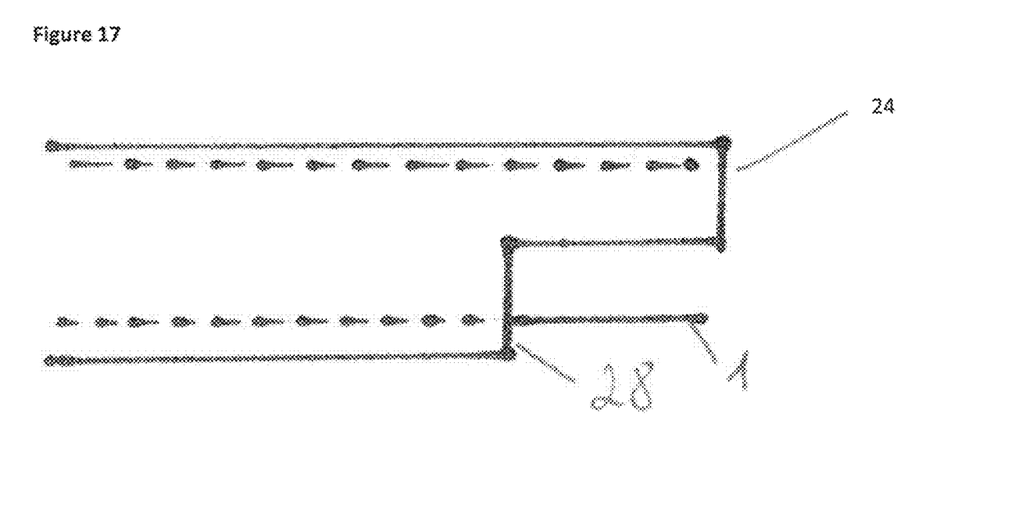
FIG. 17 shows the distal part of an exemplary embodiment of an inventive sonotrode.

It is possible that the sonotrode may include a sleeve 24 as described for the sonotrode shown in FIGS. 15 and 17.

FIG. 17 shows the distal part of a sonotrode 1. Around the sonotrode 1 is attached a sleeve 24. The sonotrode 1 may be each sonotrode according to the present invention. It is preferred that the sonotrode is located symmetrically within the sleeve. The sonotrode may have a symmetrical cross section. The sleeve may have a window at the distal end so that only a part of the sonotrode protrudes out of the sleeve. Alternatively the sleeve may be completely or partly (concerning only a part of the cross section) retractable. The part of the sonotrode protruding out of the sleeve can be used to punch out bone.

Figure 18:
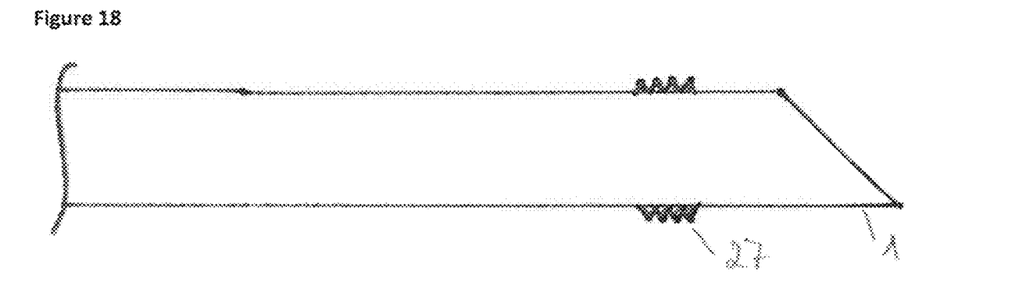
FIG. 18 shows a longitudinal section of an exemplary embodiment of an inventive sonotrode.

FIG. 18 shows a longitudinal section of a sonotrode 1 according to the invention. It illustrates that behind a distance used for punching structures 27 may be attached, which are suitable for rasping or scratching bone. They may be further be suitable for cutting into bone by moving the sonotrode along a longitudinal direction. It is preferably possible to remove or ablate bone by back and/or forth movement (bidirectional movement in regard to the surgeon). As shown the structure 27 may be circumferential ribs which may have a triangular cross section or a rectangular cross section. Alternatively these structure may be formed like spikes or spirals.

Figure 19:
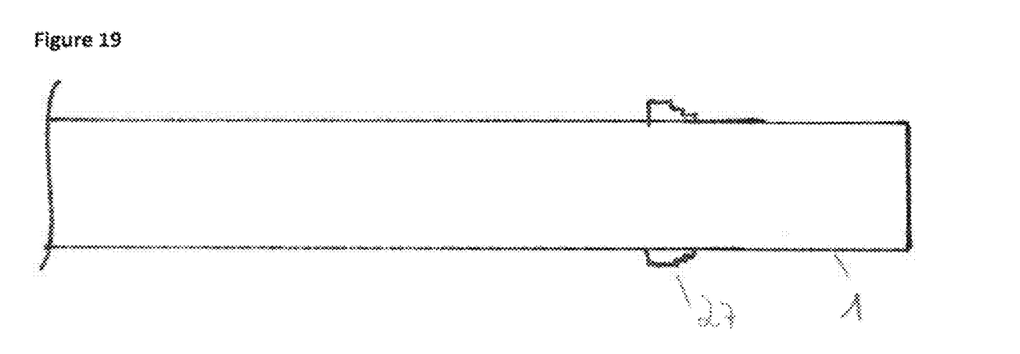
FIG. 19 shows a longitudinal section of an exemplary embodiment of an inventive sonotrode.

FIG. 19 shows a longitudinal section of a sonotrode 1 according to the invention having a structure 27 formed by several rectangular bands being attached circumferential and in a way forming a structure 27 having several steps.

Figure 20:
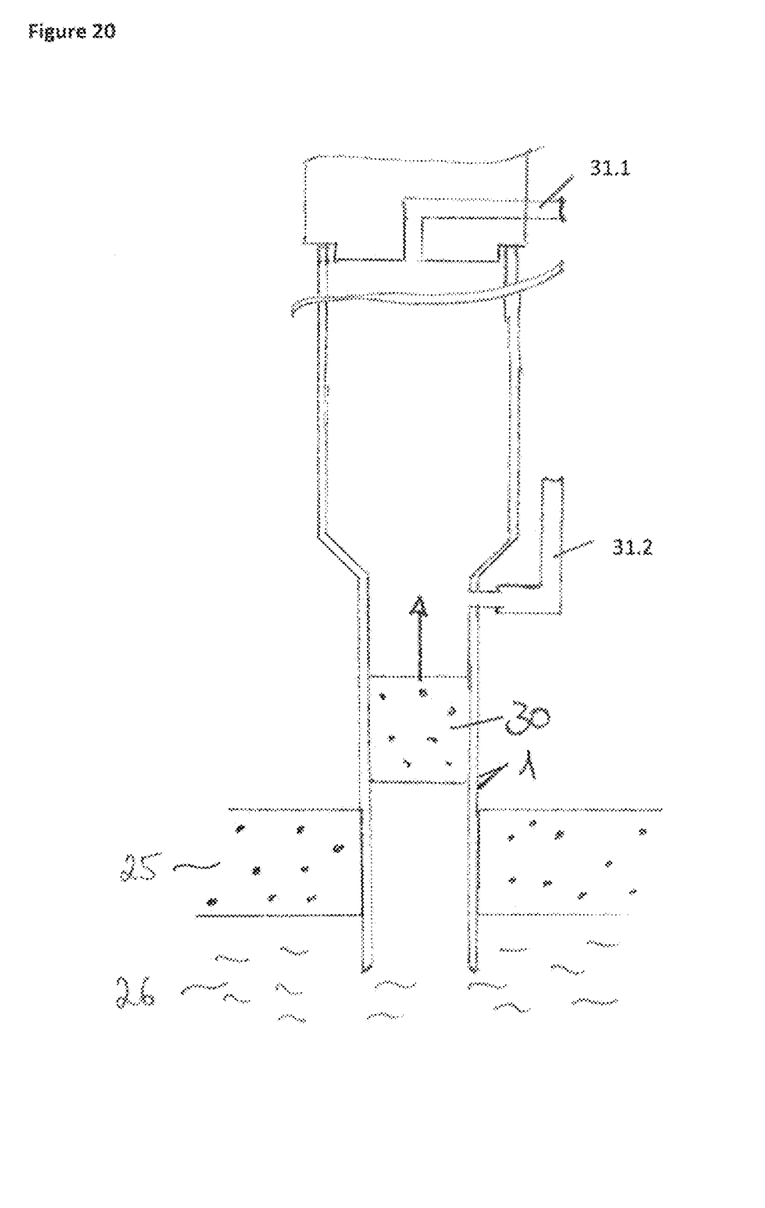
FIG. 20 shows an exemplary embodiment of an inventive sonotrode.

FIG. 20 shows a further embodiment of a sonotrode suitable for the device according to the invention. The sonotrode is particularly suitable for creating a series of bone openings before being removed from the operation site, and for removal of bone tissue (in particular the complete bone fragments punched out) from the openings created using the device. Bone fragments 30 punched out of a bone opening created with the aid of the sonotrode 1 may be stored within the hollow sonotrode or a space within the sonotrode, which may be formed by an extended cross section of the sonotrode. Thus the sonotrode may include a space suitable as depot for bone fragments 30 or bone debris. The sonotrode 1 may be designed as a disposable item, suitable to create several bone openings within one operation side and store the resulting (stamped or punched out) bone fragments. After removal from the operation side the bone fragments may be used as sample for tests or as allogenic transplant material. The sonotrode may be thrown away (with or without the bone fragments) or may easily be cleaned. The embodiment may be designed so that the vibration of the sonotrode facilitates transport of the bone fragments 30 and retain them within the open space.

In another embodiment the bone fragments may further be transported using hydraulic pressure. Therefore, there may be a channel within the device supplying a liquid such as water from the handle to the sonotrode. This liquid flow can be stopped or reversed to generate negative pressure. Alternatively, the liquid may be used to transport (or eject) the bone fragment out of the sonotrode. The bone fragment can be ejected into the operation side and flush away using the liquid generally used to clean the operation side (e.g., from blood). When using this alternative the liquid flow into the sonotrode is not stopped, but in the moment the sonotrode cuts into the bone the outflow of the liquid is stopped. Therefore, the pressure within the sonotrode increases and this pressure can be used to remove the bone fragment from the sonotrode. In case that a negative pressure is used to transport and store bone fragments punched out, the bone fragments are suctioned. This supports the process of breaking away the portion of the dense bone punched out. Therefore, it is possible to remove the bone within the cutting edge of the sonotrode in one piece and without less damage to the surrounding tissue.

The liquid fed through the instrument may further be used to cool the sonotrode and/or to rinse the operation side. A space between the sonotrode and a cannula or guide shaft may be used to suck liquid and debris of the bone out of the operational site.

A further embodiment of the sonotrode 1 for removal of bone tissue (in particular the complete bone fragments punched out) from the bone openings created using the sonotrode the sonotrode may be designed so that vacuum facilitates transport of the bone fragments 30 and retains them within the sonotrode 1. Therefore, there may be a channel 31.1 within the head of the sonotrode for pulling out air and applying vacuum within the sonotrode. This channel 31.1 may be created to run along the longitudinal axis of the sonotrode. The channel may leave the sonotrode or the housing of the sonotrode lateral. This means the proximal part of the channel 31.1 runs perpendicular to the longitudinal axis and the distal part of the channel. Alternatively, a channel 31.2 may be attached to a flange that protrudes from the sonotrode 1 and in particular its hollow end piece. At the height where the flange protrudes from the sonotrode a peripheral groove may be located within the sonotrode wall. This groove extends once around the complete circumference. It is preferred that the channel 31.1 or 31.2 is attached to the instrument in a node position (λ/4). A channel 31.1 comprised within the sonotrode head and perhaps the handle or housing has to be cleaned after each operation (each treatment of a patient). A channel 31.2 integrated in the distal end piece of the sonotrode 1 has the advantage that it has not be cleaned in case the sonotrode is a disposable item or is easier to clean because it is very short and without bend structure. On the other side it is more expensive to include such a channel in the sonotrode, in particular in case that it is a disposable item. The vacuum may also be used to support or facilitate breaking away the portion of the dense bone punched out. Therefore, it is possible to remove the bone within the cutting edge in one piece and with less damage to the surrounding tissue.

The distal end piece of the hollow sonotrode according to the invention may have ribs on its inner side. These ribs may run parallel to the longitudinal axis of the sonotrode and along the complete length or are arranged only in a distal part. The ribs may alternatively form spirals or curves on the inner side of the distal end piece of the sonotrode. The ribs or protruding spikes or alternative protruding elements attached to the inner side of the sonotrode may facilitate breaking away of bone fragments after introduction of the sonotrode into the dense bone. Therefore, the sonotrode or the complete device has to be rotated, so that torsion is applied to the bone fragment within the sonotrode. Alternatively, slicing elements may be arranged within the tube or sonotrode. These elements are suitable for cutting or breaking the bone core into small fragments respectively bone debris, which may be aspirate from the sonotrode. The slicing elements may be formed as thin blades (e.g., two, three, four or five blades), which are arranged in a way to meet one another at the central axis of the tube. The sonotrode may cut into the dense bone with its distal end and when cutting deeper into the bone the slicing elements chop the bone core into smaller fragments. The distal ends of the slicing elements or blades may be sharp and may be slanting.

What is claimed is:

1. A sonotrode for an ultrasonic surgical instrument being suitable for punching out tissue areas from bone, wherein the sonotrode has a head and a distal end piece, the distal end piece being equipped as a stamp for penetration of bones using mechanical vibration, wherein the sonotrode has at least two lateral ribs running along a longitudinal axis of the sonotrode, the at least two lateral ribs being located inside of the distal end piece.

2. The sonotrode according to claim 1, wherein the distal end piece comprises a blade whose distal cutting edge corresponds to the contour of a tissue area that is to be punched out.

3. The sonotrode according to claim 1, wherein the distal end piece or the blade is designed as a hollow body being open at its distal end.

4. The sonotrode according to claim 3, wherein the hollow body is not rotationally symmetric.

5. The sonotrode according to claim 3, wherein the hollow body is a hollow elliptic cylinder.

6. The sonotrode according to claim 1, wherein the sonotrode has one lateral rib arranged outside of the distal end piece.

7. The sonotrode according to claim 1, wherein the sonotrode has two lateral ribs arranged outside of the distal end piece.

8. The sonotrode according to claim 1, wherein the at least two lateral ribs run only along the distal end piece of the sonotrode.

9. The sonotrode according to claim 1, wherein the at least two lateral ribs each have a flattened distal end.

10. The sonotrode according to claim 1, wherein the surface of the sonotrode or the surface of the blade has a roughness average Ra between 5-40 µm.

11. The sonotrode according to claim 1, wherein the sonotrode or at least the blade of the sonotrode are manufactured using an additive manufacturing method such as direct metal laser sintering.

12. An ultrasonic surgical instrument for cutting bones, comprising a hand-piece containing an ultrasonic transducer and a sonotrode as defined in claim 1 mechanically coupled to said transducer.

13. A sonotrode for an ultrasonic surgical instrument, wherein the sonotrode has a head and a distal end piece, the distal end piece being equipped as a punch for penetration of bones or as a blade for cutting and the distal end piece has a maximal diameter being at least one and a half times the size of the diameter of the head, wherein the sonotrode has at least two lateral ribs running along a longitudinal axis of the sonotrode, the at least two lateral ribs being located inside of the distal end piece or the blade.

14. The sonotrode according to claim 13, wherein the distal end piece has a maximal diameter being at least three times the size of the diameter of the head.

15. The sonotrode according to claim 13, further comprising a sleeve with a window which allows that only a part of the distal end of the sonotrode protrudes out of the sleeve.

16. The sonotrode according to claim 13, wherein the distal end piece comprises the blade whose distal cutting edge corresponds to the contour of a tissue area that is to be punched out.

17. The sonotrode according to claim 13, wherein the distal end piece comprises an intermediate element.

18. The sonotrode according to claim 17, wherein the intermediate element comprises through holes.

19. The sonotrode according to claim 13, wherein the distal end piece has a sharpened distal edge as cutting edge.

20. The sonotrode according to claim 13, wherein the surface of the sonotrode or the surface of the blade has a roughness average Ra between 5-40 μm.

21. The sonotrode according to claim 13, wherein the sonotrode or at least the blade of the sonotrode are manufactured using an additive manufacturing method such as direct metal laser sintering.

\* \* \* \* \*